United States Patent [19]

Schickaneder et al.

[11] Patent Number: 4,559,344
[45] Date of Patent: Dec. 17, 1985

[54] PYRIDINE-PYRIMIDINONE DERIVATIVES, A PROCESS FOR THEIR PRODUCTION AND H$_2$-ANTAGONIST MEDICAMENT CONTAINING THESE COMPOUNDS

[75] Inventors: Helmut Schickaneder, Eckental; Peter Mörsdorf, Cadolzburg; Stefan Postius, Nuremberg; Istvan Szelenyi, Schwaig; Rolf Herter; Herbert Hansen, both of Schwabach; Kurt H. Ahrens, Nuremberg, all of Fed. Rep. of Germany

[73] Assignee: Ludwig Heumann & Co. GmbH, Nuremberg, Fed. Rep. of Germany

[21] Appl. No.: 574,077

[22] Filed: Jan. 26, 1984

[30] Foreign Application Priority Data

Feb. 22, 1983 [DE] Fed. Rep. of Germany ....... 3306102

[51] Int. Cl.$^4$ ................... A61K 31/505; C07D 239/02
[52] U.S. Cl. ..................... 514/269; 544/319; 546/276; 548/518; 549/28; 549/59
[58] Field of Search ......................... 544/319; 424/251; 514/269

[56] References Cited

FOREIGN PATENT DOCUMENTS 2734070 2/1978 Fed. Rep. of Germany .

OTHER PUBLICATIONS

Price et al., Chem. Abst. 88: 190580b, eqit. Ger. Offen. '070.
Brown, Chem. Abst. 100: 68313t.
Stables et al., Chem. Abst. 98: 191553p.
Clitherow et al., Chem. Abst. 92: 181197n.
Brown et al., Chem. Abst. 92: 76539c.

Primary Examiner—Donald G. Daus
Assistant Examiner—Cecilia Shen
Attorney, Agent, or Firm—Burns, Doane, Swecker & Mathis

[57] ABSTRACT

The invention relates to new pyridine-pyrimidinone derivatives corresponding to the following general formula

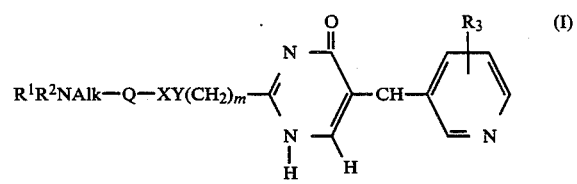

wherein
$R^1$ represents linear $C_{1-6}$ alkyl or cycloalkyl and $R^2$ represents linear $C_{1-6}$ alkyl or $R^1$ and $R^2$ together with the nitrogen atom form a pyrrolidine or piperidine ring;
Alk represents a linear alkylene chain $C_{1-6}$;
Q represents a benzene ring, furan ring, thiophene ring or thiazole ring;
X represents oxygen, Y is a single bond and m is 2, 3 or 4 when Q represents benzene;
X represents methylene, Y represents sulfur and m is 2 or 3 when Q is furan, thiophene or thiazole; and
$R^3$ represents a hydrogen atom or a lower alkyl group.

These compounds show improved H$_2$-antagonistic activity.

35 Claims, No Drawings

PYRIDINE-PYRIMIDINONE DERIVATIVES, A PROCESS FOR THEIR PRODUCTION AND H₂-ANTAGONIST MEDICAMENT CONTAINING THESE COMPOUNDS

DESCRIPTION

This invention relates to new pyridine-pyrimidinone derivatives having a strong selective effect on histamine-$H_2$-receptors, to a process for their production, to medicaments containing these compounds and, finally, to the use of these compounds for therapeutic purposes.

Cimetidine (Tagamet ®) has already been used in the treatment of ulcers. Unfortunately, cimetidine has a relatively short half life. Because of this, tablets containing doses of 200 to 300 mg in a therapeutically established form have to be administered several times a day. Accordingly, there is a need for anti-ulcer agents which are more active and/or remain active for a longer period than cimetidine.

By virtue of their specific $H_2$-antagonistic activity, the compounds obtainable in accordance with the invention inhibit the secretion of gastric acid when it is stimulated by histamine agonists [Ash and Schild, "Brit. J. Pharmacol. Chemother", 27, 427 (1966) and Black et al., "Nature", 236, 385 (1971)]. The pharmacological activity of these compounds, which will be described in more detail hereinafter, may be demonstrated by a modified method according to DE-OS No. 27 34 070 in perfused rats' stomachs. In addition, the $H_2$-antagonistic effect can be demonstrated on female Heidenhain-Pouch dogs using the method of Black et al., "Nature", 236, 385 (1971). In addition, the new compounds antagonize the effect of histamine on the frequency of contraction of the isolated right atrium of guinea pigs, but have no effect on histamine-induced contractions of the isolated, smooth gastroentestinal muscle where they are produced by $H_2$-agonists. Since inhibitors for histamine-$H_2$-receptors have an inhibiting effect both in regard to basal gastric acid secretion and also in regard to the secretion of gastric acid induced by gastrin, histamine, methacholine or food, they may be used in the treatment of peptic ulcers caused by the excessive secretion of gastric acid and also in the treatment of hyperacidic gastritis.

The object of the present invention is to provide new inhibitors for histamine-$H_2$-receptors having an improved and/or longer lasting effect.

This object is achieved by the invention.

The pyridine-pyrimidinone derivatives according to the invention may be present in the following tautomeric forms

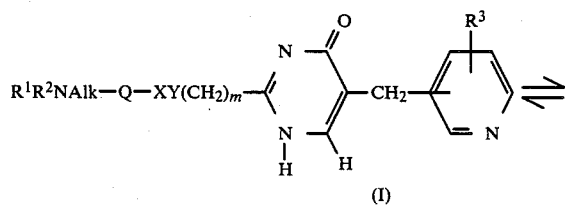

(I)

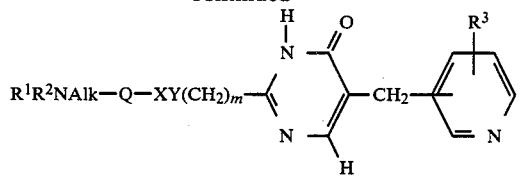

(Ia)

In formulae I and Ia, $R^1$ represents linear $C_{1-6}$ alkyl or cycloalkyl, $R^2$ represents linear $C_{1-6}$ alkyl or $R^1$ and $R^2$ together with the nitrogen atom to which they are attached form a 5- or 6-membered ring;

Alk represents a linear alkylene chain containing from 1 to 6 carbon atoms;

Q represents a benzene ring which is incorporated into the remainder of the molecule in the 1- and 3-position or in the 1- and 4-position; or Q represents a furan or thiophene ring which is incorporated into the remainder of the molecule by bonds in the 2- and 5-position; or Q represents a thiophene or thiazole ring which is incorporated into the remainder of the molecule by bonds in the 2- and 4-position;

X represents oxygen, Y represents a single bond and m has the value 2, 3 or 4 where Q represents benzene;

X represents methylene, Y represents sulfur and m has the value 2 or 3 where Q represents furan, thiophene or thiazole;

$R^3$ represents a hydrogen atom or an alkyl group in the ortho- meta- or para-position to the nitrogen atom in the pyridine ring, the methylene group being attached to the pyridine ring independently of $R^3$ in the ortho- meta- or para-position to the nitrogen atom.

The invention also relates to the physiologically compatible salts of these derivatives.

The invention covers all tautomeric forms of the derivatives according to the invention and their salts corresponding to formulae I and Ia.

One preferred group of compounds according to the invention is characterized in that $R^1$ represents $C_{1-3}$-alkyl or $C_{5-6}$-cycloalkyl and $R^2$ represents methyl or ethyl or $R^1R^2N$ represent a 5- or 6-membered ring, more particularly a piperidine ring.

Other preferred groups of compounds according to the invention are characterized in that Q represents a benzene ring which is incorporated into the remainder of the molecule by bonds in the 1- and 3-position or in the 1- and 4-position and in that the group $XY(CH_2)_m$ represents $O(CH_2)_{2-4}$, or in that Q represents a furan or thiophene ring which is incorporated into the remainder of the molecule by bonds in the 2- and 5-position and in that the group $XY(CH_2)_m$ represents $CH_2-S-(CH_2)_{2-3}$, or in that Q represents a thiophene or thiazole ring which is incorporated into the remainder of the molecule by bonds in the 2- and 4-position and in that the group $XY(CH_2)_m$ represents $CH_2-S-(CH_2)_{2-3}$.

In general formula I, $R^1$ represents a linear $C_{1-6}$, preferably $C_{1-3}$, alkyl group and, more particularly, a methyl or ethyl group or a cycloalkyl group, preferably a $C_{5-6}$-cycloalkyl group. $R^2$ represents a linear $C_{1-6}$, preferably $C_{1-3}$, alkyl group and more particularly a methyl or ethyl group. The substituents $R^1$ and $R^2$ may be selected independently of one another from the groups indicated. $R^1$ and $R^2$, together with the nitrogen atom to which they are attached, may also form a 5- or 6-membered ring, for example a pyrolidine or piperidine ring, a piperidine ring being preferred.

Alk represents a linear alkylene chain containing from 1 to 6 carbon atoms, preferably from 1 to 3 carbon atoms, and more particularly a methylene group.

Q represents a benzene, furan, thiophene or thiazole ring. The benzene ring may be incorporated into the remainder of the molecule by bonds in the 1- and 3-position or in the 1- and 4-position. Compounds in which the benzene ring is incorporated in the 1- and 3-position are preferred.

The furan ring is incorporated into the remainder of the molecule by bonds in the 2- and 5-position. The thiophene ring may be incorporated into the remainder of the molecule by bonds in the 2- and 5-position or in the 2- and 4-position, the 2- and 4-position being preferred.

The thiazole ring is incorporated into the remainder of the molecule by bonds in the 2- and 4-position.

Where Q represents a benzene ring, X is an oxygen atom and Y a single bond. In this case, m has the value 2, 3 or 4.

Where Q represents a furan, thiophene or thiazole ring, X represents the methylene group and Y a sulfur atom. In this case, m has the value 2 or 3.

$R^3$ represents a hydrogen atom or a lower alkyl group, the alkyl group being attached in the ortho-, meta- or para-position to the nitrogen atom of the pyridine ring. Compounds in which $R^3$ represents methyl and is attached in the ortho-position to the nitrogen atom of the pyridine ring are preferred.

The methylene group may be substituted in the ortho-, meta- or para-position to the nitrogen atom of the pyridine ring, irrespective of the position of the substituent $R^3$. Compounds in which the methylene group is attached in the meta-position and $R^3$ in the ortho-position to the nitrogen atom of the pyridine ring (3- or 6-position in the pyridine ring) are preferred.

The compounds according to the invention are produced by a process which is characterized in that a compound corresponding to the following general formula

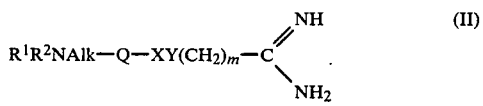

in which $R^1$, $R^2$, Alk, Q, X, Y and m are as defined above, are reacted in known manner with a pyridine derivative corresponding to the following formula

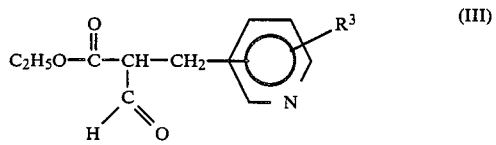

in which $R^3$ is as defined above, and the compound obtained is optionally converted into a physiologically compatible salt thereof.

In this process, a compound corresponding to general formula II is reacted with a pyridine derivative corresponding to general formula III in a base-catalyzed reaction to form the required compounds (A. Sitte et al., Chem. Ber. 102, 615 (1969)).

The reaction is carried out in a solvent and at a temperature in the range from room temperature to the boiling temperature of the solvent used. Suitable solvents are, for example, alcohols, such as methanol or ethanol, ethers, such as dioxane or tetraydrofuran. The reaction product is worked up in known manner, for example by concentrating the reaction mixture, followed by crystallization.

The compounds according to the invention may be converted with suitable acids into their physiologically compatible salts. The reaction is carried out in known manner.

Suitable acids are inorganic and organic acids. Examples of inorganic acids are hydrochloric acid, hydrobromic acid, sulfuric acid, sulfamic acid, phosphoric acid, nitric acid. Examples of suitable organic acids are maleic acid, fumaric acid, succinic acid, oxalic acid, malic acid, benzoic acid, methane sulfonic acid, ethane disulfonic acid, benzene sulfonic acid, acetic acid, propionic acid, tartaric acid, citric acid, camphor sulfonic acid and the like. In principle, any pharmaceutically suitable inorganic and organic acids may be used for conversion into the physiologically compatible salt.

It is also clear that some of the compounds of formula I disclosed herein form disalts, trisalts etc.

Preferred compounds are, for example, 5-(6-methylpyrid-3-ylmethyl)-2-[4-[3-(1-piperidylmethyl)-phenoxy]-butyl]-pyrimidin-4-one, 5-(6-methylpyrid-3-ylmethyl)-2-[4-[3-(N,N-dimethylaminomethyl)-phenoxy]-butyl]-pyrimidin-4-one, 5-(6-methylpyrid-3-ylmethyl)-2-[3-[3-(1-piperidylmethyl)-phenoxy]-propyl]-pyrimidin-4-one and the physiolocially compatible salts thereof.

The compounds according to the invention, preferably in the form of a salt, may be formulated in any way for administration. Accordingly, the invention also relates to medicaments containing at least one compound according to the invention for use in human or veterinary medicine. The medicaments according to the invention may be conventionally produced using one or more pharmaceutically compatible vehicles or diluents.

Accordingly, the compounds according to the invention may be formulated for oral, buccal, topical, parenteral or rectal administration, oral administration being preferred. For oral administration, the medicament may be present, for example, in the form of tablets, capsules powders, solutions, syrups or suspensions which have been conventionally produced using acceptable diluents. For buccal administration, the medicament may assume the form of tablets or capsules which have been conventionally formulated.

The compounds according to the invention may be formulated for parenteral administration by bolus injection or continuous infusion. Formulations for injection may be present in unit dose form as ampoules in multiple-dose containers with added preservative.

The medicaments may assume such forms as suspensions, solutions or emulsions in oily or aqueous vehicles and may contain formulation aids, such as suspending agents, stabilizers and/or dispersants. Alternatively, the active principle may even be present in powder form for reconstitution before use with a suitable vehicle, for example sterile, pyrogen-free water.

The compounds according to the invention may also be formulated for rectal preparations, for example suppositories or retention enemas containing, for example, conventional suppository bases, such as cocoa butter or other glycerides.

For topical application, the compounds according to the invention may be conventionally formulated as ointments, creams, gels, lotions, powders or sprays.

For oral administration, a suitable daily dose of compounds according to the invention is from 1 to 4 doses containing a total of up to 5 mg to 1 g per day and preferably 5 to 250 mg per day, depending on the condition of the patient. In individual cases, it may be necessary to vary the dosage in dependence upon the reaction of the individual to the active principle or its formulation and upon the time at which or intervals at which it is administered. For example, there are cases where it will be sufficient to administer less than the minimum dose specified above, whereas in other cases the dose administered will have to exceed the upper limit indicated.

The compounds according to the invention are distinguished from recognized medicaments acting in the same direction by an improvement in the pharmacological activity levels. This is apparent from the results of the comparative pharmacological studies reported hereinafter.

A recognized method of measuring $H_2$-antagonistic activity is based on determination of the $pA_2$-values in vitro on the isolated atrium of guinea pigs (cf. Ariens, Molecular Pharmacology, Vol. 1, Academic Press, New York, 1964).

| | $pA_2$-values | |
|---|---|---|
| Cimetidine: | 6.21 | comparison |
| Example 1 | 7.66 | |

Other compounds corresponding to general formula I show similar pharmacological activity.

EXAMPLE 1

5-(6-methylpyrid-3-ylmethyl)-2-[4-[3-(1-piperidylmethyl)-phenoxy]-butyl]-pyrimidin-4-one

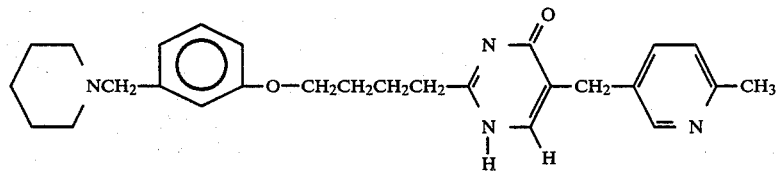

A solution of 2.2 g (10 mmoles) of 2-formyl-3-(6-methyl-3-pyridyl)-propionic acid ethyl ester in 20 ml of ethanol is added to a solution of 0.67 g (10 mmoles) of sodium ethylate in 20 ml of ethanol. After the addition of 3.53 g (12.2 mmoles) of 5-[3-(1-piperidylmethyl)-phenoxy]-valeroamidine in 10 ml of ethanol, the mixture is stirred for 48 hours at room temperature, the solvent is concentrated in vacuo and the residual oil taken up in 30 ml of water. The aqueous solution is extracted three times with 20 ml of chloroform, the organic phase is dried over sodium sulfate, filtered and the solvent removed in vacuo. The residual oil crystallizes after rubbing.

Colorless crystals melting at 113° C.
$R_f = 0.3$ ($CH_2Cl_2/CH_3OH$ 90:10)
Yield: 2.85 g (64%)
$C_{27}H_{34}N_4O_2$ (447)

| $^1$H—NMR-spectrum: (CDCl$_3$, TMS as internal standard) | $\delta$ = 1.20–2.44 (m) 14 H, |
|---|---|
| | 2.46 (s) (Py—$\underline{CH_3}$) 3 H, |
| | 2.71 (t) (—$\underline{CH_2}$—CH$_2$—CH$_2$O) 2 H, |
| | 3.40 (s) ($>$N—$\underline{CH_2}$—) 2 H, |
| | 3.68 (s) (—$\underline{CH_2}$—Py) 2 H, |
| | 3.98 (t) (—O—$\underline{CH_2}$—) 2 H, |
| | 6.62–7.60 (m) (aromatic-$\underline{H}$) 6 H |
| | 7.82 (s) (Py—$\underline{H}$) 1 H, |
| | 8.48 (s) (Py—$\underline{H}$) 1 $\underline{H}$ ppm. |

EXAMPLE 1a

Production of 5-[3-(1-piperidylmethyl)-phenoxy]-valeroamidine dihydrochloride 3.0 g (10 mmoles) of methyl-5-[3-(1-piperidylmethyl)-phenoxy]-valeroimidate and 0.54 g (10 mmoles) of ammonium chloride are stirred in 20 ml of methanol for 24 hours at room temperature. After extensive concentration, 3.3 ml (~20 mmoles) of ethanolic hydrochloric acid are added and the dihydrochloride formed is precipitated with ether.

Colorless crystals melting at 178°–180° C.
$R_f = 0.6$ ($CH_3OH$)
Yield: 3.1 g (85%)

| $C_{17}H_{29}Cl_2N_3O$ (362) | Calculated: | C 56.35 | H 8.07 | N 11.60 |
|---|---|---|---|---|
| | Observed: | C 56.44 | H 8.02 | N 11.53 |

EXAMPLE 1b

Production of 2-formyl-3-(6-methyl-3-pyridyl)-propionic acid ethyl ester (a) Production of 6-methyl-3-pyridine aldehyde 80 g (0.37 mole) of sodium periodate in 200 ml of water are added dropwise with vigorous stirring to 23 g (0.19 mole) of 2-methyl-5-vinyl pyridine in 800 ml of ethylene glycol dimethyl ether. 1.0 g (0.04 mole) of osmium tetroxide is then added while cooling with a mixture of ice and common salt, after which the mixture is stirred for 8 hours at room temperature in a nitrogen atmosphere. The oil remaining after removal of the solvent by evaporation in vacuo is taken up in a little water and extracted three times with ethyl acetate. Drying of the organic phase over sodium sulfate and concentration by evaporation in vacuo leave 20 g (87%) of a light brown oil which is immediately further processed.

(b) Production of 3-(6-methyl-3-pyridyl)-acrylic acid ethyl ester 1.5 ml of piperidine are added to a solution of 25 g (0.19 mole) of malonic acid monoethyl ester in 50 ml of pyridine, followed by the dropwise addition of 17 g (0.14 mole) of 6-methyl-3-pyridine aldehyde. The mixture is refluxed for 5 hours and, after cooling, is poured onto a mixture of ice and concentrated hydrochloric acid. After extraction by shaking with diethyl ether, the organic phase is dried over sodium sulfate and concentrated by evaporation in vacuo, leaving 17.8 g (67%) of the title compound in the form of an oil which is further processed without purification.

(c) Production of 3-(6-methyl-3-pyridyl)-propionic acid ethyl ester 17.8 g (0.092 mole) of 3-(6-methyl-3-pyridyl)-acrylic acid ethyl ester in 100 ml of ethanol are hydrogenated at 40° C./atmospheric pressure in the presence of 1.0 g of palladium/active carbon (10% Pd). On completion of the reaction, the reaction mixture is filtered and the solvent is concentrated in vacuo, leaving 16.2 g (90%) of a colorless oil.

(d) Production of 2-formyl-3-(6-methyl-3-pyridyl)-propionic acid ethyl ester A mixture of 16.0 g (0.083 mole) of 3-(6-methyl-3-pyridyl)-propionic acid ethyl ester and 9.6 g (0.13 mole) of formic acid ethyl ester is slowly added dropwise while cooling with ice to a suspension of 5.2 g of sodium hydride (80% on paraffin oil; 0.17 mole) in 30 ml of ethylene glycol dimethyl ether. On completion of the addition, the solution is stirred for 8 hours at room temperature. After the addition of 10 ml of ethyl acetate and 200 ml of ice water, the mixture is extracted three times with diethyl ether. The aqueous phase is diluted to pH 5.4 with dilute hydrochloric acid and the crystals precipitating are filtered under suction. Light brown crystals melting at 141°–142° C. are obtained in a yield of 12.8 g (70%).

EXAMPLE 2

5-(6-methylpyrid-3-ylmethyl)-2-[3-[3-(1-piperidylmethyl)-phenoxy]-propyl]-pyrimidin-4-one.

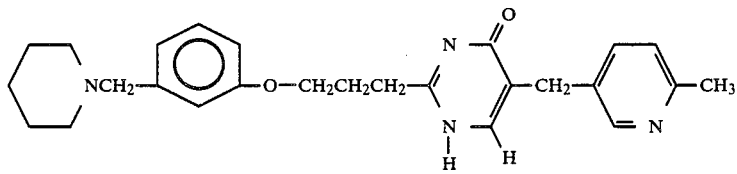

A solution of 2.2 g (10 mmoles) of 2-formyl-3-(6-methyl-3-pyridyl)-propionic acid ethyl ester in 20 ml of ethanol is added to a solution of 0.67 g (10 mmoles) of sodium ethylate in 20 ml of ethanol. After the addition of 3.38 g (12.2 mmoles) of 4-[3-(1-piperidylmethyl)-phenoxy]-butyroamidine in 10 ml of ethanol, the mixture is stirred for 48 hours at room temperature, the solvent is evaporated off in vacuo and the residual oil is taken up in 30 ml of water. The aqueous solution is extracted three times with 20 ml of chloroform, the organic phase is dried over sodium sulfate, filtered and the solvent removed in vacuo. The residual oil crystallizes after rubbing.

Colorless crystals melting at 139° C.
Rf=0.2 (CH$_2$Cl$_2$/CH$_3$OH 90:10)
Yield: 3.89 g (90%)

| C$_{26}$H$_{32}$N$_4$O$_2$ (433) | Calculated: | C 72.19 | H 7.46 | N 12.95 |
|---|---|---|---|---|
| | Observed: | C 72.17 | H 7.47 | N 13.02 |

$^1$H—NMR-spectrum: (CDCl$_3$, TMS as internal standard)

δ = 1.15–2.60 (m) 12 H, 2.48 (s) (Py—CH$_3$) 3 H, 2.82 (t) (—O—CH$_2$CH$_2$CH$_2$) 2 H, 3.37 (s) (⟩N—CH$_2$) 2 H 3.70 (s) (Py—CH$_2$) 2 H, 4.02 (t) (—O—CH$_2$—) 2 H, 6.55–7.63 (m) (aromatic-H) 6 H, 7.82 (s) (Py—H) 1 H, 8.47 (s) (Py—H) 1 H, 11.3 (broad) (—NH) 1 H (exchangeable for D$_2$O) ppm.

EXAMPLE 2a

4-[3-(1-piperidylmethyl)-phenoxy]-butyroamidine is produced as in Example 1a from methyl-4-[3-(1-piperidylmethyl)-phenoxy]-butyrimidate and ammonium chloride. Colorless crystals melting at 162° C.

EXAMPLE 3

5-(pyrid-4-ylmethyl)-2-[4-[3-(1-piperidylmethyl)-phenoxy]-butyl]pyrimidin-4-one

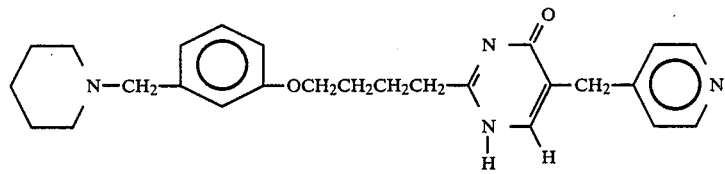

This compound is produced as in Example 2 from 2.9 g (10 mmoles) of 5-[3-(1-piperidylmethyl)p-phenoxy]-valeroamidine and 1.65 g (8 mmoles) of 2-formyl-3-(4-pyridyl)-propionic acid ethyl ester. The oil obtained crystallizes after rubbing with a little ethyl acetate.

Colorless crystals melting at 105.5° C.
$R_f=0.4$ (CH$_2$Cl$_2$/CH$_3$OH 50:50)
Yield: 1.8 g (52%)

| C$_{26}$H$_{32}$N$_4$O$_2$ (432) | Calculated: | C 72.19 | H 7.46 | N 12.95 |
| --- | --- | --- | --- | --- |
| | Observed: | C 72.29 | H 7.47 | N 13.04 |

$^1$H—NMR-spectrum:
(CDCl$_3$, TMS as internal standard)

δ = 1.35–2.48 (m) 14 H, 2.71 (t) (—CH$_2$CH$_2$CH$_2$CH$_2$O—) 2 H, 3.42 (s) (>N—CH$_2$) 2 H, 3.73 (s) (—CH$_2$Py) 2 H, 3.99 (t) (—O—CH$_2$—) 2 H, 6.67–7.30 (m) (aromatic-H) 6 H, 7.87 (s)

8.48–8.60 (m) (Py—H) 2 H ppm.

EXAMPLE 3a

Production of 2-formyl-3-(4-pyridyl)-propionic acid ethyl ester (a) Production of 3-(4-pyridyl)-acrylic acid ethyl ester 21.2 g (60%) of 3-(4-pyridyl)-acrylic acid ethyl ester in the form of an oil are obtained as in Example 1b from 36.8 g (0.28 mole) of malonic acid monoethyl ester and 21.4 g (0.2 mole) of 4-pyridine aldehyde.

(b) Production of 3-(4-pyridyl)-propionic acid ethyl ester

The hydrogenation of 21 g (0.12 mole) of 3-(4-pyridyl)-acrylic acid ester in 100 ml of ethanol in the presence of palladium/active carbon (1.0 g, 10% Pd) at 40° C. and atmospheric pressure gives 20.4 g (95%) of a pale brown oil.

(c) Production of 2-formyl-3-(4-pyridyl)-propionic acid ethyl ester

The formylation of 20.4 g (0.11 mole) of 3-(4-pyridyl)-propionic acid ethyl ester with 12.7 g (0.17 mole) of formic acid ethyl ester as in Example 1b gives 9.5 g (40%) of the title compound in the form of light brown crystals melting at 135° C.

EXAMPLE 4

2-[2-[5-(N,N-dimethylaminomethyl)-furan-2-ylmethyl-thio]-ethyl]-5-(6-methylpyrid-3-ylmethyl)-pyrimidin-4-one

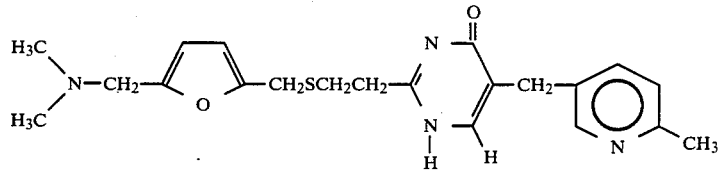

3 ml of triethylamine are added to a solution of 1.2 g (5.5 mmoles) of 2-formyl-3-(6-methyl-3-pyridyl)-propionic acid ethyl ester and 2.1 g (9 mmoles) of 3-[5-(N,N-dimethylaminomethyl)-furan-2-ylmethylthio]-propionamidine in 50 ml of ethanol. After stirring for 48 hours at room temperature, the mixture is refluxed for 1 hour. The oil remaining after concentration of the solvent in vacuo is taken up in 20 ml of water and the aqueous phase is extracted three times with 20 ml of chloroform. After drying over sodium sulfate, the organic phase is filtered and concentrated by evaporation. The residual oil crystallizes on rubbing with ether.
Colorless crystals melting at 163° C.
$R_f=0.25$ (CH$_3$OH)
Yield: 1.7 g (79%)

| C$_{21}$H$_{26}$N$_4$O$_2$S (398) | Calculated: | C 63.29 | H 6.58 | N 14.06 |
| --- | --- | --- | --- | --- |
| | Observed: | C 63.05 | H 6.59 | N 14.44 |

$^1$H—NMR-spectrum:
(CDCl$_3$, TMS as internal standard)

δ = 2.26 (s) (CH$_3$—N—) 6 H,
   CH$_3$ 2.48 (s) (Py—CH$_3$) 3 H,
2.57–3.05 (m) (—S—CH$_2$—CH$_2$—) 4 H, 3.42 (s) ( \N—CH$_2$—) 2 H, 3.72 (s) (Py—CH$_2$—), —CH$_2$S—) 4 H
6.12 (s) (furan-H) 2 H,
7.00–7.58 (m) (Py—H) 2 H,
7.76 (s)
8.4–8.47 (s)
10.7 (broad) (—NH) 1 H ppm.

EXAMPLE 4a

3-[5-(N,N-dimethylaminomethyl)-furan-2-ylmethyl-thio]-propionamidine is produced as in Example 1a from methyl-3-[5-(N,N-dimethylaminomethyl)-furan-2-ylmethylthio]-propionimidate and ammonium chloride.
Colorless crystals melting at 135°–136° C.

EXAMPLE 5

5-(6-methylpyrid-3-ylmethyl)-2-[4-[3-(N,N-dimethylaminomethyl)-phenoxy]-butyl]-pyrimidin-4-one

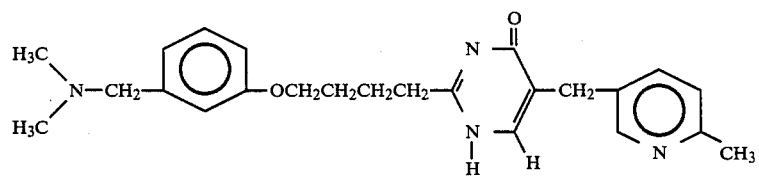

This compound is obtained as in Example 2 from 2.5 g (10 mmoles) of 5-[3-(N,N-dimethylaminomethyl)-phenoxy]-valeroamidine and 1.65 g (8 mmoles) of 2-formyl-3-(6-methyl-3-pyridyl)-propionic acid ethyl ester. The residual oil is purified by chromatography on silica gel using methylene chloride/methanol 1:1. After removal of the eluent by evaporation, the main fraction gives a light yellow oil which crystallizes after rubbing with ethyl acetate.

Colorless crystals melting at 109° C.
$R_f=0.3$ (CH$_2$Cl$_2$/CH$_3$OH 1:1)
Yield: 0.8 g (25%)

| C$_{24}$H$_{30}$N$_4$O$_2$ (407) | Calculated: | C 70.91 | H 7.44 | N 13.78 |
| | Observed: | C 70.87 | H 7.42 | N 13.82 |

$^1$H—NMR-spectrum: (CDCl$_3$, TMS as internal standard)
$\delta = 1.72-2.12$ (m) 4 H,
2.21 (s) (CH$_3$\N—) 6 H,
     /CH$_3$
2.47 (s) (Py—CH$_3$) 3 H,
2.72 (t) (—O—CH$_2$CH$_2$CH$_2$CH$_2$—) 2 H,
3.37 (s) (\N—CH$_2$—) 2 H,
        /
3.70 (s) (Py—CH$_2$) 2 H,
4.00 (t) (—O—CH$_2$—) 2 H
6.70-7.58 (m) (aromatic-H) 6 H,
7.83 (s) 1 H,
8.47 (s) (Py—H) 1 H ppm.

EXAMPLE 6

2-[3-[2-(N,N-dimethylaminomethyl)-thiazolyl-4-methylthio]-propyl]-5-(6-methylpyrid-3-ylmethyl)-pyrimidin-4-one

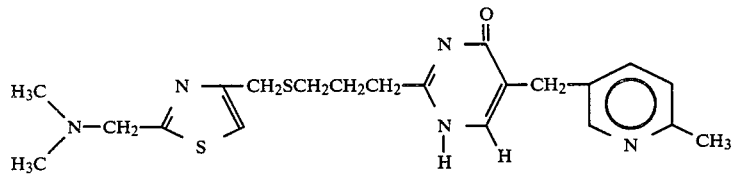

This compound is produced as in Example 4 from 2.7 g (10 mmoles) of 4-[2-(N,N-dimethylaminomethyl)-thiazolyl-4-methylthio]-butyroamidine and 2.0 g (9.5 mmoles) of 2-formyl-3-(6-methyl-3-pyridyl)-propionic acid ethyl ester.

Colorless crystals melting at 109° C.
$R_f=0.6$ (CH$_2$Cl$_2$/CH$_3$OH 50:50)
Yield: 1.8 g (44%)

| C$_{21}$H$_{27}$N$_5$OS$_2$ (430) | Calculated: | C 58.71 | H 6.33 | N 16.30 |
| | Observed: | C 58.63 | H 6.30 | N 16.23 |

$^1$H—NMR-spectrum: (CDCl$_3$, TMS as internal standard)
$\delta = $
1.84-2.23 (m) (—S—CH$_2$—CH$_2$—CH$_2$—) 2 H,
2.32 (s) (H$_3$C\N—) 6 H,
        /H$_3$C
2.48 (s) (Py—CH$_3$) 3 H,
2.57-2.88 (m) (—S—CH$_2$—CH$_2$—CH$_2$) 4 H, 3.71 (s)  ⎫ (\N—CH$_2$—,         2 H
3.74 (s)  ⎬  /                    2 H
3.82 (s)  ⎭  Py—CH$_2$—CH$_2$S—)  2 H 7.02-7.61 (m) (aromatic-H) 3 H,
7.80 (s) 1 H,
8.43 (s) (Py—H) 1 H ppm.

EXAMPLE 7

2-[2-[5-(N,N-dimethylaminomethyl)-furan-2-ylmethylthio]-ethyl]-5-(pyrid-3-ylmethyl)-pyrimidin-4-one

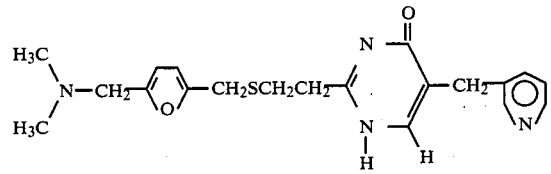

A yellowish oil which crystallizes after rubbing with ethyl acetate is obtained as in Example 4 from 2.4 g (10 mmoles) of 3-[5-(N,N-dimethylaminomethyl)-furan-2-ylmethylthio]-propionamidine and 1.65 g (8 mmoles) of 2-formyl-3-(3-pyridyl)-propionic acid ethyl ester.

Colorless crystals melting at 105° C.
$R_f=0.3$ (CH$_3$OH)
Yield: 1.9 g (62%)
C$_{20}$H$_{24}$N$_4$O$_2$S (384.5)

$^1$H—NMR-spectrum: (CDCl$_3$, TMS as internal standard)
$\delta = 2.26$ (s) ((CH$_3$)$_2$N—) 6 H,
2.61-3.09 (m) (—S—CH$_2$—CH$_2$—) 4 H,
3.42 (s) (\N—CH$_2$—) 2 H,
        /
3.73 (s) ⎫
3.77 (s) ⎬ (Py—CH$_2$—CH$_2$S—) 2 H,
                                2 H,
6.12 (s) (furan-H) 2 H,
7.14-7.75 (m) (Py—H) 2 H,
7.80 (s) 1 H,
8.45-8.64 (m) (Py—H) 2 H,
11.5 (broad) (—NH) 1 H ppm.

EXAMPLE 8

5-(pyrid-3-ylmethyl)-2-[4-[3-(1-piperid methyl)-phenoxy]-butyl]-pyrimidin-4-one

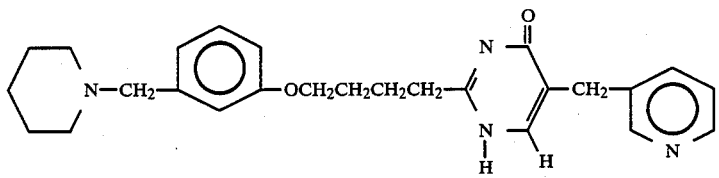

For purification, the oil obtained as in Example 2 from 2.9 g (10 mmoles) of 5-[3-(1-piperidylmethyl)-phenoxy]-valeroamidine and 1.65 g (8 mmoles) of 2-formyl-3-(3-pyridyl)-propionic acid ethyl ester is chromatographed with methylene chloride/methanol 4:1 on silica gel. After removal of the eluent by evaporation, the main fraction gives a colorless oil which is crystallized with n-hexane.

Colorless crystals melting at 78° to 79° C.
$R_f=0.4$ ($CH_2Cl_2/CH_3OH$ 4:1)
Yield: 2.1 g (60%)
$C_{26}H_{32}N_4O_2$ (432.6)

$^1H$—NMR-spectrum: $\delta = 1.28$–2.54 (m) 14 H,
(CDCl$_3$, TMS as internal standard)

2.73 (t) (—OCH$_2$CH$_2$CH$_2$CH$_2$—) 2 H, 3.45 (s) ($\rangle$N—CH$_2$—) 2 H, 3.73 (s) (Py—CH$_2$—) 2 H, 3.98 (t) (—O—CH$_2$) 2 H 6.70–7.70 (m) (aromatic-H) 6 H, 7.85 (s) 1 H, 8.41–8.65 (m) (Py—H) 2 H, 12.20 (broad) (—NH) 1 H ppm.

EXAMPLE 9

2-[3-[2-(1-piperidylmethyl)-thienyl-4-methylthio]-propyl]-5-(pyrid-3-ylmethyl)-pyrimidin-4-one

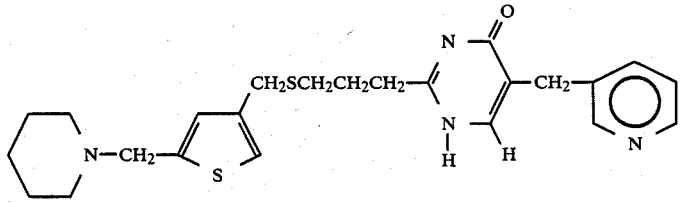

The title compound is produced as in Example 4 from 3.1 g (10 mmoles) of 4-[2-(1-piperidylmethyl)-thienyl-4-methylthio]-butyroamidine and 2.1 g (10 mmoles) of 2-formyl-3-(3-pyridyl)-propionic acid ethyl ester. After purification by chromatography with methylene chloride/methanol 9:1 on silica gel, the main fraction is concentrated by evaporation and rubbed with ethyl acetate.

Colorless crystals melting at 88° C.
$R_f=0.3$ ($CH_2Cl_2/CH_3OH$ 4:1)
Yield: 2.0 g (44%)
$C_{24}H_{30}N_4OS_2$ (454)

$^1H$—NMR-spectrum: $\delta = 1.37$–2.90 (m) 16 H,
(CDCl$_3$, TMS as internal standard)

3.62 (s)  $\rangle$( N—CH$_2$—, Py—CH$_2$, 2 H
3.64 (s)                                    2 H
3.75 (s)  $\rangle$—CH$_2$S—)              2 H, 6.87 (s) (thiophene-H) 1 H,
6.95 (s) (thiophene-H) 1 H,
7.12–7.73 (m) (Py—H) 2 H,
7.84 (s) 1 H,
8.43–8.67 (m) (Py—H) 2 H,
12.6 (broad) (—NH) 1 H ppm.

EXAMPLE 10

5-(pyrid-3-ylmethyl)-2-[4-[4-(1-piperidylmethyl)-phenoxy]-butyl]-pyrimidin-4-one

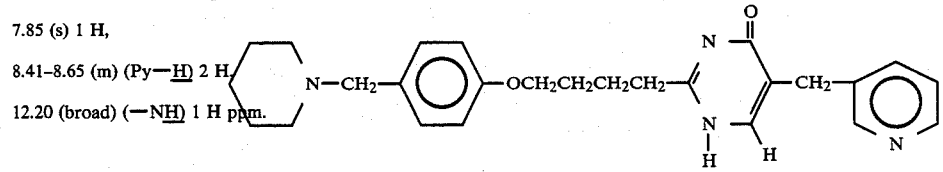

A yellow oil is obtained as in Example 2 from 2.2 g (7.5 mmoles) of 5-[4-(1-piperidylmethyl)-phenoxy]-valeroamidine and 1.55 g (7.5 mmoles) of 2-formyl-3-(3-pyridyl)-propionic acid ethyl ester and is purified by chromatography with methylene chloride/methanol 2:1 on silica gel.

Colorless oil
$R_f=0.2$ ($CH_2Cl_2/CH_3OH$ 2:1)
Yield: 1.6 g (50%)

| | |
|---|---|
| $C_{26}H_{32}N_4O_2$ (432) | δ = 1.40–2.60 (m) 14 H, |
| $^1H$—NMR-spectrum: (CDCl₃, TMS as internal standard) | 2.73 (t) (—O—CH₂CH₂CH₂CH₂—) 2 H, |
| | 3.52 (s) (⟩N—CH₂—) 2 H, |
| | 3.75 (s) (Py—CH₂—) 2 H, |
| | 3.98 (t) (—O—CH₂—) 2 H, |
| | 6.75–7.70 (m) (aromatic-H) 6 H, |
| | 7.85 (s) 1 H, |
| | 8.41–8.64 (m) (Py—H) 2 H, |
| | 11.5 (broad) (—NH) 1 H ppm. |

We claim:

1. Pyridine-pyrimidinone compounds corresponding to the following formula

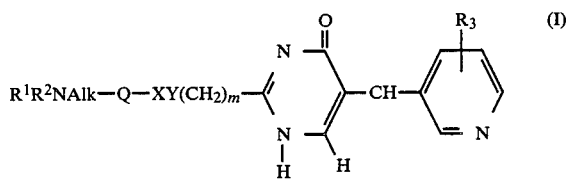

in which
R¹ represents linear $C_{1-6}$ alkyl or cycloalkyl and
R² represents linear $C_{1-6}$ alkyl or
R¹ and R² together with the nitrogen atom to which they are attached form a pyrrolidine or piperidine ring;
Alk represents a linear alkylene chain containing from 1 to 6 carbon atoms;
Q represents a benzene ring which is incorporated in the remainder of the molecule by bonds in the 1- and 3-position or in the 1- and 4-position, or
Q represents a furan ring which is incorporated into the remainder of the molecule by bonds in the 2- and 5-position or
Q represents a thiophene ring which is incorporated into the remainder of the molecule by bonds in the 2- and 5-position or in the 2- and 4-position or
Q represents a thiazole ring which is incorporated into the remainder of the molecule by bonds in the 2- and 4-position;
X represents oxygen, Y is a single bond and m has the value 2, 3 or 4 where Q represents benzene;
X represents methylene, Y represents sulfur and m has the value 2 or 3 where Q is furan, thiophene or thiazole;
R³ represents a hydrogen atom or a lower alkyl group; and physiologically compatible salts thereof.

2. Compounds as claimed in claim 1, characterized in that R¹ represents $C_{1-3}$ alkyl or $C_{5-6}$ cycloalkyl and R² represents methyl or ethyl or R¹ R²N form a 5- to 6-membered ring.

3. Compounds as claimed in claim 1 or 2, characterized in that the group Alk represents methylene.

4. Compounds as claimed in any of claims 1 to 3, characterized in that Q represents a benzene ring which is incorporated into the remainder of the molecule by bonds in the 1- and 3-position or in the 1- and 4-position, and in that the group $XY(CH_2)_m$ represents $O(CH_2)_{2-4}$.

5. Compounds as claimed in any of claims 1 to 3, characterized in that Q represents a furan or thiophene ring which is incorporated into the remainder of the molecule by bonds in the 2- and 5-position and in that the group $XY(CH_2)_m$ represents —CH₂—S—(CH₂)₂₋₃.

6. Compounds as claimed in any of claims 1 to 3, characterized in that Q represents a thiophene or thiazole ring which is incorporated into the remainder of the molecule by bonds in the 2- and 4-position and in that the group $XY(CH_2)_m$ represents $CH_2$—S—$(CH_2)_{2-3}$.

7. Compounds as claimed in any of claims 1 to 6, characterized in that the methylene group is attached to the pyridine ring in the ortho, meta or para-position.

8. Compounds as claimed in claim 7, characterized in that the methylene group is attached to the pyridine in the meta-position, to the nitrogen atom.

9. Compounds as claimed in any of claims 1 to 7, characterized in that R³ represents a hydrogen atom or an alkyl group, with the proviso that, as an alkyl group, R³ is attached in the ortho, meta or para-position.

10. Compounds as claimed in claim 8, characterized in that R³ is attached in the ortho-position, to the nitrogen atom in the pyridine ring.

11. 5-(6-methylpyrid-3-ylmethyl)-2-[4-[-3-(1-piperidylmethyl)-phenoxy]-butyl]-pyrimidin-4-one and the physiologically compatible salts thereof.

12. 5-(6-methylpyrid-3-ylmethyl)-2-[4-[3-(N,N-dimethylaminomethyl)-phenoxy]-butyl]-pyrimidin-4-one and the physiologically compatible salts thereof.

13. 5-(pyrid-3-ylmethyl)-2-[4-[3-(1-piperidylmethyl)-phenoxy]-butyl]-pyrimidin-4-one and the physiologically compatible salt thereof.

14. 5-(pyrid-4-ylmethyl)-2-[4-[3-(1-piperidylmethyl)-phenoxy]-butyl]-pyrimidin-4-one and the physiologically compatible salts thereof.

15. 5-(pyrid-2-ylmethyl)-2-[4-[3-(1-piperidylmethyl)-phenoxy]-butyl]-pyrimidin-4-one and the physiologically compatible salts thereof.

16. 5-(6-methylpyrid-3-ylmethyl)-2-[3-[3-(1-piperidylmethyl)-phenoxy]-propyl]-pyrimidin-4-one and the physiologically compatible salts thereof.

17. 5-(6-methylpyrid-3-ylmethyl)-2-[4-[4-(1-piperidylmethyl)-phenoxy]-butyl]-pyrimidin-4-one and the physiologically compatible salts thereof.

18. 5-(6-methylpyrid-3-ylmethyl)-2-[4-[4-(N,N-dimethylaminomethyl)-phenoxy]-butyl]-pyrimidin-4-one and the physiologically compatible salts thereof.

19. 5-(pyrid-3-ylmethyl)-2-[4-[4-(1-piperidylmethyl)-phenoxy]-butyl]-pyrimidin-4-one and the physiologically compatible salts thereof.

20. 5-(6-methylpyrid-3-ylmethyl)-2-[3-[4-(1-piperidylmethyl)-phenoxy]-propyl]-pyrimidin-4-one and the physiologically compatible salts thereof.

21. 2-[2-[5-(N,N-dimethylaminomethyl)-furan-2-ylmethylthio]-ethyl]-5-(6-methylpyrid-3-ylmethyl)-pyrimidin-4-one and the physiologically compatible salts thereof.

22. 2-[3-[5-(N,N-dimethylaminomethyl)-furan-2-ylmethylthio]-propyl]-5-(6-methylpyrid-3-ylmethyl)-pyrimidin-4-one and the physiologically compatible salts thereof.

23. 2-[2-[5-(N,N-dimethylaminomethyl)-furan-2-ylmethylthio]-ethyl]-5-(pyrid-3-ylmethyl)-pyrimidin-4-one and the physiologically compatible salts thereof.

24. 2-[3-[5-(N,N-dimethylaminoethyl)-furan-2-ylmethylthio]-propyl]-5-(pyrid-3-ylmethyl)-pyrimidin-4-one and the physiologically compatible salts thereof.

25. 2-[2-[2-(N,N-dimethylaminomethyl)-thienyl-4-methylthio]-ethyl]-5-(6-methylpyrid-3-ylmethyl)-pyrimidin-4-one and the physiologically compatible salts thereof.

26. 5-(6-methylpyrid-3-ylmethyl)-2-[3-[2-(1-piperidylmethyl)-thienyl-4-methylthio]-propyl]-pyrimidin-4-one and the physiologically compatible salts thereof.

27. 2-[3-[2-(1-piperidylmethyl)-thienyl-4-methylthio]-propyl]-5-pyrid-3-ylmethyl)-pyrimidin-4-one and the physiologically compatible salts thereof.

28. 5-(6-methylpyrid-3-ylmethyl)-2-[2-[2-(1-piperidylmethyl)-thienyl-4-methylthio]-ethyl]-pyrimidin-4-one and the physiologically compatible salts thereof.

29. 2-[2-[2-(1-piperidylmethyl)-thienyl-4-methylthio]-ethyl]-5-pyrid-3-ylmethyl)-pyrimidin-4-one and the physiologically compatible salts thereof.

30. 5-(6-methylpyrid-3-ylmethyl)-2-[2-[2-(1-piperidylmethyl)-thienyl-5-methylthio]-ethyl]-pyrimidin-4-one and the physiologically compatible salts thereof.

31. 5-(6-methylpyrid-3-ylmethyl)-2-[3-[2-(1-piperidylmethyl)-thienyl-5-methylthio]-propyl]-pyrimidin-4-one and the physiologically compatible salts thereof.

32. 2-[2-[2-(N,N-dimethylaminomethyl)-thiazolyl-4-methylthio]-ethyl]-5-(6-methylpyrid-3-ylmethyl)-pyrimidin-4-one and the physiologically compatible salts thereof.

33. 2-[3-[2-(N,N-dimethylaminomethyl)-thiazolyl-4-methylthio]-propyl]-5-(6-methylpyrid-3-ylmethyl)-pyrimidin-4-one and the physiologically compatible salts thereof.

34. A $H_2$-antagonist medicament, characterized in that it contains an effective amount of a compound of the type claimed in claim 1 and at least one inert, pharmaceutically compatible vehicle or an inert, pharmaceutically compatible diluent.

35. A $H_2$-antagonist medicament as claimed in claim 34, characterized in that together with at least one other active ingredient.

* * * * *